(12) United States Patent
Gliner et al.

(10) Patent No.: US 6,178,357 B1
(45) Date of Patent: Jan. 23, 2001

(54) ELECTRODE PAD SYSTEM AND DEFIBRILLATOR ELECTRODE PAD THAT REDUCES THE RISK OF PERIPHERAL SHOCK

(75) Inventors: Bradford E. Gliner, Issaquah, WA (US); Stephen M. Dillon, New York, NY (US); Kent W. Leyde, Redmond, WA (US)

(73) Assignee: Agilent Technologies, Inc., Palo Alto, CA (US)

( * ) Notice: Under 35 U.S.C. 154(b), the term of this patent shall be extended for 0 days.

(21) Appl. No.: 09/143,701

(22) Filed: Aug. 28, 1998

(51) Int. Cl.$^7$ ..................................... A61N 1/05
(52) U.S. Cl. .......................... 607/142; 607/152; 600/392; 600/393; 600/587
(58) Field of Search .................... 607/115, 142, 607/148, 149, 152, 153; 600/372, 382, 386, 391, 392, 393, 587

(56) References Cited

U.S. PATENT DOCUMENTS

| | | |
|---|---|---|
| 4,267,576 | * 5/1981 | Power et al. . |
| 4,419,998 | 12/1983 | Heath . |
| 4,483,103 | 11/1984 | Bickel . |
| 4,653,503 | 3/1987 | Heath . |
| 4,681,112 | 7/1987 | Jones et al. . |
| 4,797,104 | * 1/1989 | Laerdal et al. .................. 434/265 |
| 4,852,585 | 8/1989 | Heath . |
| 4,895,169 | 1/1990 | Heath . |
| 4,955,381 | 9/1990 | Way et al. . |
| 4,979,517 | 12/1990 | Grossman et al. . |
| 5,080,099 | 1/1992 | Way et al. . |
| 5,137,458 | 8/1992 | Ungs et al. . |
| 5,184,620 | 2/1993 | Cudahy et al. . |
| 5,330,526 | 7/1994 | Fincke et al. . |
| 5,352,315 | 10/1994 | Carrier et al. . |
| 5,466,244 | 11/1995 | Morgan . |
| 5,571,165 | 11/1996 | Ferrari . |
| 5,782,238 | 7/1998 | Beitler . |
| 5,951,598 | * 9/1999 | Bishay et al. ......................... 607/142 |
| 5,993,219 | * 11/1999 | Bishay .................................. 607/142 |

OTHER PUBLICATIONS

R2 Medical System electrode pads.
Physio Control Quik–Combo™ electrode pads.
Zoll Medical Corporation stat•padz™.
Cardiotronics Multi–Pads™.
Laerdal Medical Heartstart® electrodes.
Contour Medical, Quantum Edge System.
Fast–Patch®, Physio–Control Disposable Defibrillation/ECG Electrodes.
Quik–Combo™, Physio–Control Disposable Pacing/Defibrillation/ECG Electrodes with Redi–Pak™.
MediTrace® 1110L, Graphic Controls Corp. Combination Defibrillation and ECG Electrode (packaging).
MediTrace® 1210H, Graphic Controls Corp. Combination Defibrillation, Pacing and ECG Electrode (packaging).

* cited by examiner

*Primary Examiner*—Kennedy Schaetzle
(74) *Attorney, Agent, or Firm*—Cecily Anne Snyder

(57) ABSTRACT

This invention is directed to a medical electrode system having a flexible substrate with two electrodes in electrical communication disposed at either end along its length. The electrode system also has one or more sensors for detecting the rate and pressure at which CPR is administered. The electrode is adjustable in length and protects the user from the potential of incidental shock when using the electrode in conjunction with a defibrillator.

20 Claims, 4 Drawing Sheets

ELECTRODE PAD SYSTEM AND DEFIBRILLATOR ELECTRODE PAD THAT REDUCES THE RISK OF PERIPHERAL SHOCK

BACKGROUND OF THE INVENTION

1. Field of the Invention

This invention relates generally to medical electrode systems and, in particular, to a defibrillator electrode system for use with an automatic or semi-automatic external defibrillator (referred to collectively as "AEDs").

2. Description of the Prior Art

One frequent consequence of heart attacks is the development of cardiac arrest associated with heart arrhythmias, such as ventricular fibrillation ("VF"). VF is caused by an abnormal and very fast electrical activity in the heart. During VF the heart cannot pump blood effectively. VF may be treated by applying an electric shock to the patient's heart through the use of a defibrillator. Defibrillation clears the heart of the abnormal electrical activity by depolarizing a critical mass of myocardial cells to allow spontaneous organized myocardial depolarization to resume, thus restoring normal function. Because blood no longer pumps effectively during VF, the chance of surviving cardiac arrest decreases with time after the arrest. Quick response to cardiac arrest by administering a defibrillating shock as soon as possible after the onset of VF is therefore often critically important.

Increasing the number of potential defibrillator operators who are trained in the proper use of an AED increases the likelihood that a trained defibrillator operator will be available during an emergency and thus could ultimately reduce the defibrillator deployment time. As the number of potential operators increases, however, the frequency with which each operator uses the skills developed during training decreases. Depending upon the amount of time since the defibrillator operator last used a defibrillator, review of electrode placement instructions will likely be required to determine correct placement of the electrode pads. Failure to apply the electrode pads correctly can reduce the amount of defibrillation energy that is applied to the myocardium. Misapplied electrodes can allow the current to flow along the chest wall, thus missing the heart, and result in a failure of the defibrillation shock. Such a review of pad placement, while necessary, delays the speed with which defibrillation can be performed on the patient. With every second that passes, the likelihood of successfully restoring the patient's heart to a normal sinus rhythm decreases. Therefore, every step in the deployment and use of a defibrillator that can be streamlined is critical.

One time saving gain has been the development of electrode pads which eliminate the step of attaching electrode pads to the cable, and, for the most part, eliminate the need to untangle the cable. An example of such an electrode system is described in U.S. Pat. No. 5,466,244 for "Defibrillator Electrode System" by Morgan. Other electrode pad designs are known in the art.

An additional concern relates to the whether the rescuer, or any other person touching the patient during shock delivery, is at risk of being shocked. It is possible, that a voltage gradient of sufficient magnitude could be generated which could shock a rescuer. In some situations such a voltage gradient could appear within 5 cm of the perimeter of a standard electrode.

Currently available defibrillator electrode pads used with AEDs use two adhesive electrode pads with an insulated backing. The two adhesive pads reduce the risk that the rescuer will be shocked by eliminating the need for direct contact with the electrodes during shock delivery. Hospital defibrillator electrodes, on the other hand, require the operator to hold the electrode paddles to the patient's chest when delivering the shock. In spite of the fact that the rescuer typically is not in contact with the patient when delivering a shock through the adhesive electrodes, there is still a concern that the area between the electrodes where the current flows could, nonetheless, increase the rescuer's shock risk.

Another problem relating to adhesive electrodes relates to proper placement. Whether electrodes are used for defibrillation, monitoring, or pacing, proper placement of the electrodes is important for collecting and assessing the most accurate patient data. For example, when defibrillator electrodes are not properly placed on the torso, the shock delivered through the heart does not travel directly through the heart and the shock is less efficacious.

Another difficulty that is encountered relates to administration of cardiopulmonary resuscitation ("CPR") in connection with defibrillation. When a lay user (e.g. police officer, fire fighter, airline attendant, or security guard) is operating a defibrillator they may be out-of-practice with the location for CPR compression (for cardiac compression). Additionally, there is currently no method for determining whether the rescuer is pressing hard enough to pump blood for the victim. CPR without correct compression, in both placement and pressure, does not effectively pump the victim's blood.

What is needed is an easy to use electrode system that reduces the risk of incidental shock to the rescuer or a bystander. What is also needed is an electrode system that shows the rescuer where to administer the CPR compressions. Additionally what is needed is an electrode system that provides life size markers for correct electrode pad placement, or additional instructions for AED usage or CPR administration. Also what is needed is an electrode system that provides additional circuitry for detecting CPR rate and force, allowing the defibrillator to use the information to provide feedback to the rescuer.

SUMMARY OF THE INVENTION

This invention is directed to a medical electrode system having a flexible substrate with two electrode disks in electrical communication disposed at either end along its length. The electrode system also has one or more sensors for detecting the rate and pressure at which CPR is administered. The electrode is adjustable in length and protects the user from the potential of incidental shock when using the electrode in conjunction with a defibrillator. The electrode is disposed on a release placard that provides a visual indication for proper placement of the electrode as well as storage opportunity for equipment that may be useful in deploying the electrode.

BRIEF DESCRIPTION OF THE DRAWINGS

FIG. 4A does not have sensors for detecting CPR rate and compression while FIG. 4B does have sensors.

FIGS. 5A and 5B differ from FIGS. 4A and 4B in construction of the flexible material. FIG. 5A differs from FIG. 5B in that FIG. 5A has sensors (similar to FIG. 4B) and FIG. 5B does not (similar to FIG. 4A).

DESCRIPTION OF THE PREFERRED EMBODIMENTS

Figure 1:
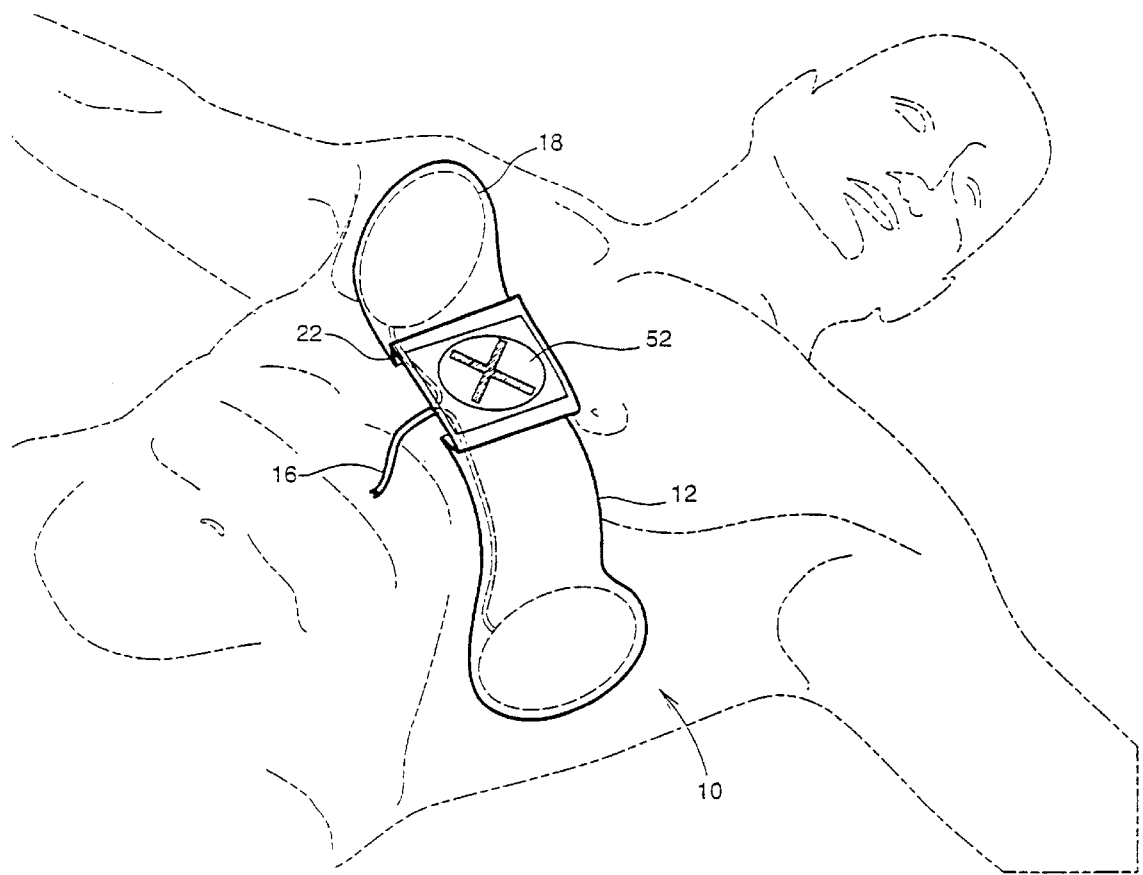
FIG. 1 is a top elevational view of an electrode of this invention as it would be positioned on a victim after deployment.

FIG. 1 shows an electrode system according to a preferred embodiment of this invention as it would be positioned on a victim after the electrode is deployed for use.

Figure 2:
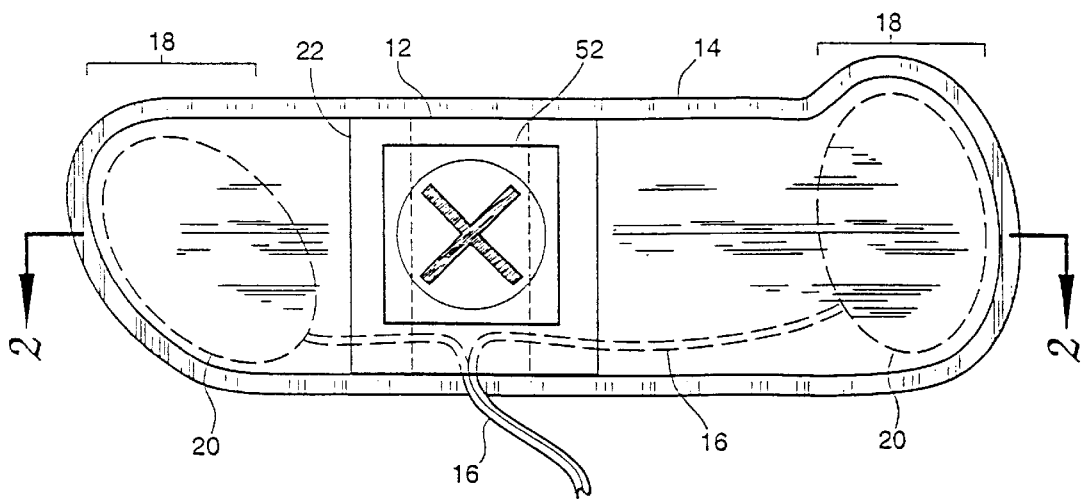
FIG. 2 is a top elevational view of an electrode system of this invention.

FIG. 2 shows the electrode system 10 with an electrode pad 12. Lead lines 16 may be incorporated into the electrode pad, so that only one lead line exits from the electrode 12 (as shown by 16'). Alternatively, each lead line 16 may exit the electrode near their respective side of the torso, before attaching to a defibrillator. The electrode pad 12 has a conductive electrode disk incorporated into an insulated conductive section 18 at either end. For purposes of illustration, the electrode disks 20 have been depicted in shadow along with lead lines 16. It will be appreciated by persons skilled in the art that the electrode disks can be of any shape. Typically, electrode disks are round, oval, or square; however, other shapes may be employed without departing from the scope of the invention. For purposes of illustration, electrode disks have been depicted as being oval in shape.

One or more folds, depicted as 22 in FIGS. 1 and 2, may be provided to allow an increase the in length of the electrode pad 12 as each fold is unfolded. By providing one or more folds, the electrode pad 12 can lengthen to fit a wide variety of victims.

Figure 3:
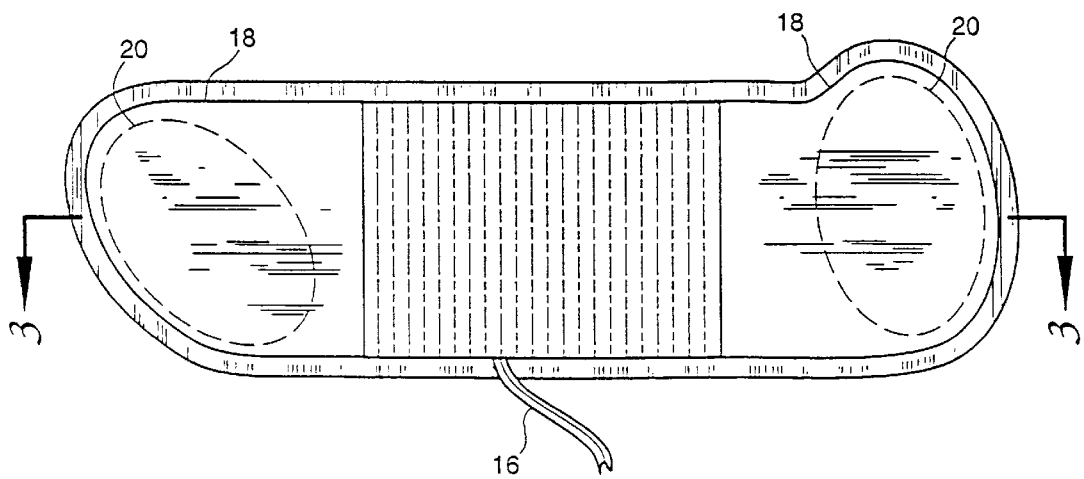
FIG. 3 is a top elevational view of an alternate embodiment of an electrode system of this invention.

As shown in FIG. 3, the electrode pad 12 may be formed so that the insulating section 24 between the insulated conductive sections 18 has elastic qualities (as shown by the dashed lines). Such elastic qualities would allow the electrode pad 12 to lengthen, as needed, to fit a variety of chest sizes. The elastic quality may be achieved in a variety of ways. For example, the section between the conductive defibrillation electrodes may be formed from a suitable elastic insulative material. Alternatively, such an elastic material may be formed using the same insulative material used at the defibrillation electrode site. The insulative foam backing may be fused or integrated within an elastic layer thus forming an elastic insulated backing material. In a preferred embodiment, the insulative material extends from 2–15 cm beyond the edge of the conductive area.

Imprinting can be provided on the electrode pad 12 itself that shows, for example, a marker indicating where CPR chest compressions should be administered 52 (see FIGS. 1 and 2). Alternatively, physiological markers (not shown) showing portions of the heart, ribs, etc. may be provided to assist the user in correctly orienting the electrode during placement. Additional instructions (also not shown) may be imprinted on the electrode pad 12 itself indicating the correct procedure for administering CPR.

Figure 4A:
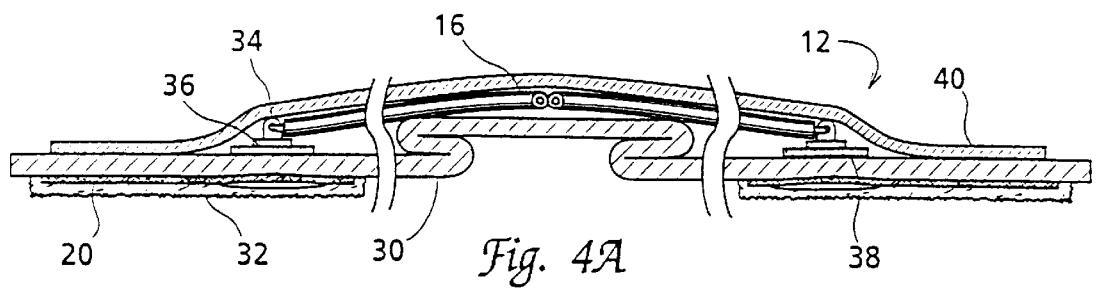
FIGS. 4A and 4B are cross-sectional side views, along the lines 2—2 in FIG. 2, of an electrode system of this invention as shown in FIG. 2.

As shown in FIG. 4A, the electrode pad 12 of FIG. 2 is formed of a flexible substrate 30, with an electrode disk 20 provided at either end of the flexible substrate. An appropriate electrode disk would be, for example, a piece of metal foil, attached to the lower surface of the flexible substrate with medical grade adhesive. Suitable metal foil would be, for example, 2-mil tin. The electrode disks are electrically connected to a lead wire 16 between the foam backing layer and the electrode disk on the upper surface of the electrode disk. The lower surface of the electrode disk is covered with a layer of conductive gel 32. A suitable conductive gel would be, for example, an RG 63T hydrogel. Additionally, the lead wires 16 may be attached to a ring terminal 34 prior to attaching to the electrode disk 20. Further, a washer 36 may be provided between the ring terminal and the electrode disk to improve the electrical connection. Finally, an insulating disk 38 may be provided between the electrode disk 20 and the washer 36.

An additional piece of flexible material 40 may be further provided covering the 30 electrode assembly, and the flexible substrate 30. Additionally, of lead wires 16 may be arranged so that they combine to form a single wire (containing both lead wires 16) at some point while the wires are located between the flexible material 40 and the flexible substrate 30.

The conductive gel layer of the electrode pad is attached to the silicone coated side of the releasing placard. Additionally, one or more pieces of separating tape, shown in FIG. 5 as 42, may be provided to ensure the easy removal of the electrode pad 12 from the releasing surface without damaging the lead wire assembly.

The area between the electrically conductive sections of the electrode pad 12 does not necessarily include an adhesive layer. For example, the area between the conductive sections could either not have adhesive material, or could have a non-conductive adhesive material.

Figure 4B:
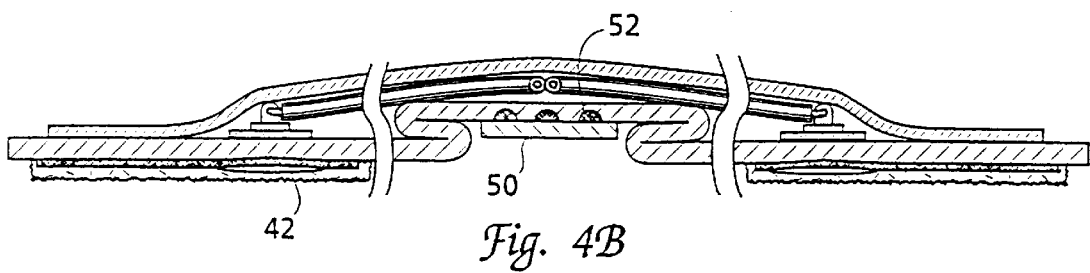

FIG. 4B depicts the electrode pad of FIG. 4A with one or more sensors 50 for detecting the amount of pressure delivered by the rescuer during CPR. The sensors 50 are capable of communicating with the defibrillator to provide information. Communication may be by direct connection, such as by connectors 52 or may be by any other suitable mechanism, for example, RF signal. The sensors may be formed of any suitable material capable of providing information regarding the amount of pressure applied, such as, for example, piezo film available from PenWalt Corp.

Figure 5A:
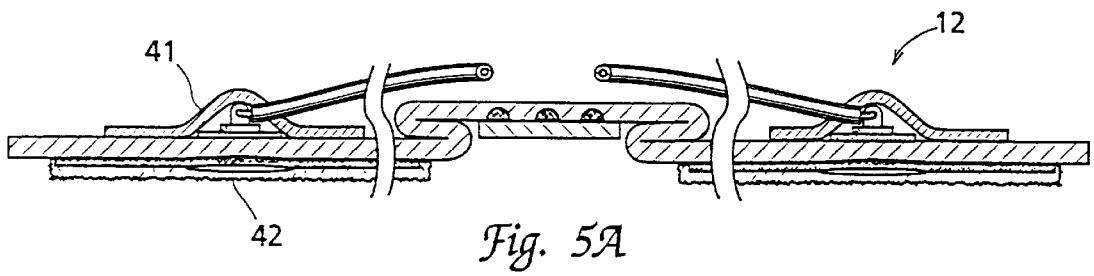
FIGS. 5A and 5B are cross-sectional side view, along the lines 2—2 in FIG. 2, of an alternative embodiment of an electrode system of this invention as shown in FIG. 2.
Figure 5B:
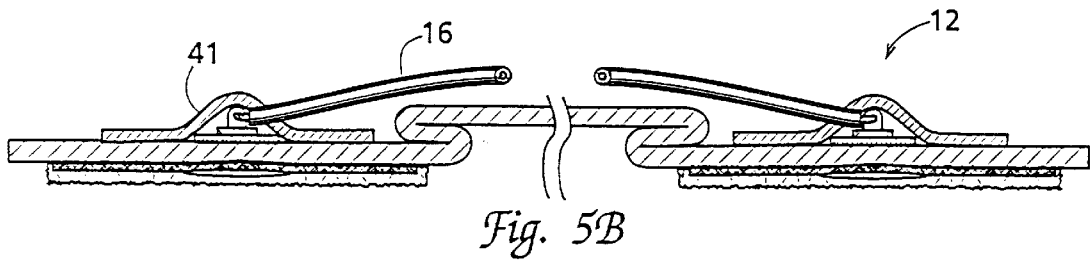

As shown in FIG. 5A, the electrode pad 12 of FIG. 2 is formed of a flexible substrate 30, an electrode disk 20 is provided at either end of the flexible substrate. As stated above, an appropriate electrode disk would be, for example, a piece of metal foil, attached to the lower surface of the flexible foam backing with medical grade adhesive. Suitable metal foil would be, for example, 2-mil tin. The electrode disks are electrically connected to a lead wire 16 between the flexible substrate and the electrode disk on the upper surface of the electrode disk. As with the construction described above, the lower surface of the electrode disk is covered with a layer of conductive gel 32. A suitable conductive gel would be, for example, an RG 63T hydrogel. Additionally, the lead wires 16 may be attached to a ring terminal 34 prior to attaching to the electrode disk 20. Further a washer 36 may be provided between the ring terminal and the electrode disk to improve the electrical connection. Finally an insulating disk 38 may be provided between the electrode disk 20 and the washer 36.

Two pieces of flexible material 41 may be further provided covering the electrode assembly, and a portion of the flexible substrate 30. Additionally, the lead wires 16 may be arranged so that they combine to form a single wire (containing both of the lead wires 16).

The conductive gel layer of the electrode pad is attached to the silicone coated side of the releasing surface. Additionally, one or more pieces of separating tape, shown in FIG. 5A as 42, may be provided to ensure the easy removal of the electrode pad 12 from the releasing surface without damaging the lead wire assembly.

The area between the electrically conductive sections of the electrode does not necessarily include an adhesive layer. For example, the area between the conductive sections could either not have adhesive material, or could have a non-conductive adhesive material.

One or more additional sensors, shown as 50, may be provided to obtain additional data to the defibrillator. As described above, the sensors are in electrical communication with the defibrillator either by connectors 52 or other suitable means. Such additional data includes, for example, compression rate or strength for CPR. Sensors would be chosen based on the information to be monitored. Suitable sensors would be known in the art and are not discussed herein.

Figure 6:
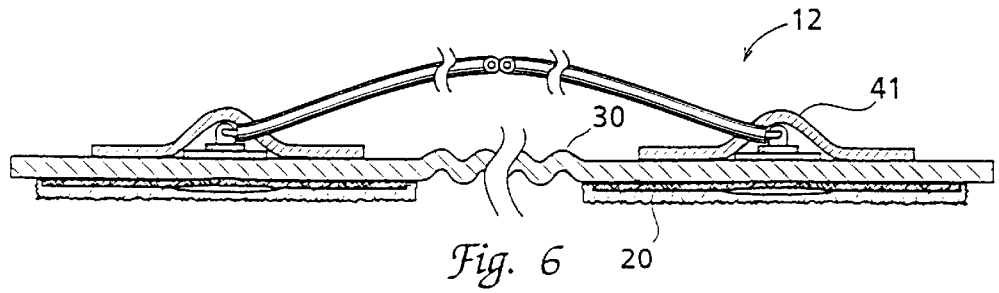
FIG. 6 is a cross-sectional side view, along the lines 3—3 in FIG. 3, of the alternate embodiment of an electrode system of this invention as shown in FIG. 3.

As shown in FIG. 6, the electrode pad 12 of FIG. 3 is formed of a flexible substrate 31, an electrode disk 20 is provided at either end of the electrode pad. Again, an appropriate electrode disk would be, for example, a piece of metal foil, attached to the lower surface of the flexible substrate with medical grade adhesive. As described above, suitable metal foil would be, for example, 2-mil tin. The electrode disks are electrically connected to a lead wire 16 between the foam backing layer and the electrode disk on the upper surface of the electrode disk. The lower surface of the electrode disk is covered with a layer of conductive gel 32. A suitable conductive gel would be, for example, an RG 63T hydrogel. Additionally, the lead wires 16 may be attached to a ring terminal 34 prior to attaching to the electrode disk 20. Further a washer 36 may be provided between the ring terminal and the electrode disk to improve the electrical connection. Finally an insulating disk 38 may be provided between the electrode disk 20 and the washer 36.

Two pieces of flexible material 41 may be further provided covering the electrode assembly. Additionally, the lead wires, 16 may be imbedded or affixed to the flexible substrate 31, thus allowing the lead wires to essenntially form a single wire (containing both lead wires 16) at some point prior to separating from the flexible substrate 31.

The conductive gel layer of the electrode pad 12 attached to the silicone coated side of the releasing surface. Additionally, one or more pieces of separating tape 42 may be provided to ensure the easy removal of the electrode pad from the releasing surface without damaging the lead wire assembly.

As with the above embodiments, additional sensors 50 may be provided to obtain additional data. Such additional information could include, for example, the compression strength and rate for CPR.

The area between the electrically conductive sections of the electrode does not necessarily include an adhesive layer. For example, the area between the conductive sections could either not have adhesive material, or could have a non-conductive adhesive material. Additionally, non-conductive adhesive material could be provided along the mid-point of the electrode.

Figure 7:
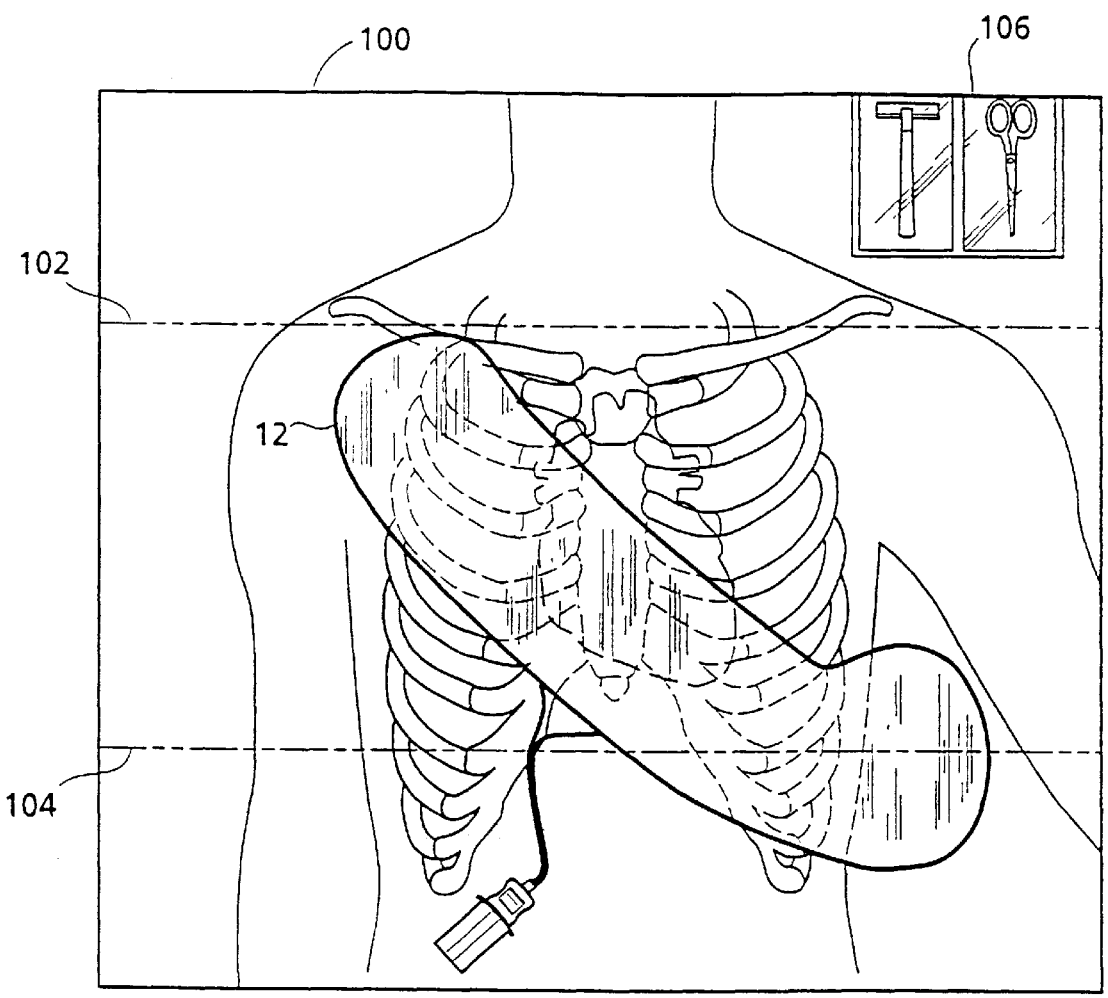
FIG. 7 is a top elevational view of an electrode of this invention adhered to a releasing placard.

FIG. 7 shows a releasing placard 100 on which the electrode 12 is removably adhered. In a preferred embodiment, the releasing placard 100 has fold lines 102/104 which enable the placard to be folded. The placard 100 also has one or more storage areas, such as pocket 106 for holding equipment that might be used when attaching the electrode, such as scissors or a razor. It will be appreciated by those of skill in the art, that the storage area need not be pockets to fall within the scope of the invention and that any other suitable mechanism for making additional equipment available would be contemplated. Additionally, the placard is printed to show a portion of the human body, as well as other information that may be of assistance to the rescuer when deploying the electrode. The electrode 12 is placed on the placard 100 such that it is situated on the image of the human body in the same manner as it would be situated on the victim. For purposes of illustration, the placard has been shown with the electrode system described above. However, as will be apparent to those skilled in the art, the placard may be used with any electrode configuration, including, but not limited to, an electrode system having two electrode disks on a single substrate (as described above) or an electrode system comprising two electrode pads. Additionally, the placard may be used with a 3-lead or 12-lead electrode set-up (typically used for cardiac monitoring).

In operation, the electrode 12 is removed from the release placard 100. The rescuer positions the electrode pad 12 so that the center portion is positioned over the victim's heart (as shown in FIGS. 1 and 7). One end of the electrode is then attached to the right aspect of the clavicle while the other end is positioned at the lower left base of the ribs toward the axial line. The rescuer may use the graphic representation on the placard to confirm correct placement of the electrode. Additionally, prior to attaching the electrode 12, the rescuer may use the scissors or razor provided in, for example, pocket 106 to remove hair from the chest of the victim in order to improve the ability of the gel to adhere to the skin of the victim.

By positioning the electrode as described, the rescuer is protected from peripheral shock. Additionally, where marking is provided on the electrode surface, the rescuer will have a marker for where to place their hands for the thrusting portion of CPR.

Modifications to the invention embodiments described above will be apparent to those skilled in the art. Such modifications are within the scope the invention.

What is claimed:

1. A defibrillator electrode system comprising an electrode pad having:
   an elongated flexible substrate adapted to be applied across a chest of a patient, the elongated flexible substrate having a first end and a second end;
   a first and a second electrode disk capable of delivering a defibrillation shock in electrical communication disposed on the elongated flexible substrate, wherein the first electrode is disposed on the elongated flexible substrate at the first end and the second electrode is disposed on the elongated flexible substrate at the second end;
   at least one sensor for detecting CPR compressions disposed on the elongated flexible substrate between the first and second electrode disk; and
   a first and a second conductive gel layer adhered to the first and second electrode disks.

2. The defibrillation electrode system of claim 1 wherein the at least one sensor detects rate at which CPR compressions are administered.

3. The defibrillation electrode system of claim 1 wherein the at least one sensor detects the force at which CPR compressions are administered.

4. The defibrillator electrode system of claim 1 wherein the electrode pad is adhered to an electrode placard having imprinting to show the proper placement of the electrode.

5. The defibrillator electrode system of claim 4 wherein the imprinting on the electrode placard includes an image of a portion of the human body.

6. The defibrillation electrode system of claim 1 wherein the electrode pad is adjustable in length.

7. The defibrillation electrode system of claim 6 wherein the electrode pad has a plurality of folded sections.

8. The defibrillation electrode system of claim 6 wherein the electrode pad has an elasticized section between the two ends of the electrode pad.

9. The defibrillation electrode system of claim 8 wherein the elasticized section is integrally formed with the flexible sections at either end.

10. The defibrillation electrode system of claim 4 wherein the imprinting on the electrode can be interpreted by an AED operator without reviewing other information.

11. The defibrillation electrode system of claim 1 wherein the electrode pad is releasable adhered to a placard.

12. The defibrillator electrode system of claim 10 wherein the placard further includes a storage area.

13. The defibrillation electrode system of claim 10 wherein the placard further includes scaled imprinting corresponding to the anatomy of a human body.

14. The defibrillation electrode system of claim 1 wherein the flexible substrate extends beyond a perimeter of the electrode disks at least 5 cm.

15. The medical electrode system of claim 14 wherein the sensor detects the rate at which CPR compressions are administered.

16. The medical electrode system of claim 14 wherein the sensor detects the force at which CPR compressions are administered.

17. A releasable placard for use in a medical electrode system comprising at least one electrode, the releasable placard having:
   a releasing surface for adhering to the at least one electrode; and
   a storage area for holding equipment to be used when the electrode system is deployed.

18. The releasable placard of claim 17 wherein at least one electrode pad is adhered thereto.

19. The releasable placard of claim 17 wherein two electrode pads are adhered thereto.

20. The releasable placard of claim 17 wherein the placard is imprinted to show a portion of the human body.

* * * * *